US006846535B2

(12) United States Patent
De Groot et al.

(10) Patent No.: US 6,846,535 B2
(45) Date of Patent: Jan. 25, 2005

(54) KINK RESISTANT MEDICAL TUBES

(75) Inventors: Hendrik De Groot, Louvain-la-Neuve (BE); Freddy Maria Armand Vervoort, Louvain-la-Neuve (BE)

(73) Assignee: Kraton Polymers U.S. LLC, Houston, TX (US)

( * ) Notice: Subject to any disclaimer, the term of this patent is extended or adjusted under 35 U.S.C. 154(b) by 2 days.

(21) Appl. No.: 10/130,371

(22) PCT Filed: Jun. 7, 2001

(86) PCT No.: PCT/EP01/06467

§ 371 (c)(1),
(2), (4) Date: Oct. 3, 2002

(87) PCT Pub. No.: WO01/94466

PCT Pub. Date: Dec. 13, 2001

(65) Prior Publication Data

US 2004/0072956 A1 Apr. 15, 2004

(30) Foreign Application Priority Data

Jun. 7, 2000 (EP) ............................................. 00202025

(51) Int. Cl.$^7$ ............................ C08L 53/02; C08L 23/10
(52) U.S. Cl. ........................ 428/36.9; 525/98; 604/19; 604/264
(58) Field of Search .................... 525/98; 428/36.9; 604/19, 264

(56) References Cited

U.S. PATENT DOCUMENTS

| 3,865,776 A | | 2/1975 | Gergen | |
|---|---|---|---|---|
| 4,196,731 A | * | 4/1980 | Laurin et al. | 600/435 |
| 4,588,777 A | * | 5/1986 | Hotta | 525/93 |
| 5,969,027 A | * | 10/1999 | Chundury et al. | 524/436 |
| 6,303,200 B1 | * | 10/2001 | Woo et al. | 428/36.9 |

FOREIGN PATENT DOCUMENTS

| EP | 0 623 651 A2 | 11/1994 |
|---|---|---|
| JP | 10-67894 | 10/1998 |

OTHER PUBLICATIONS

Masa et al., electronic translation of JP 10–067894, Oct. 1998.*

* cited by examiner

*Primary Examiner*—Jeffrey Mullis

(57) ABSTRACT

Kink resistant medical tube is manufactured from a polymer composition comprising:
a) a random polypropylene copolymer; and
b) a block copolymer comprising at least two vinyl aromatic polymer blocks and at least one hydrogenated conjugated diene polymer block, wherein the hydrogenated conjugated diene polymer block has a vinyl content before hydrogenation of at least 50%.

18 Claims, No Drawings

KINK RESISTANT MEDICAL TUBES

This application takes priority from European Patent Application Serial No. 00202025.3, filed Jun. 7, 2000, and International Application No. PCT/EP01/06467, filed Jun. 7, 2001, both of which are assigned to the assignee of this application.

BACKGROUND OF THE INVENTION

1. Field of the Invention

The present invention relates to medical tubes that are resistant to kinking when bent and have a commercially acceptable degree of transparency. The invention further relates to polymer compositions that are useful in manufacturing these medical tubes.

2. Background of the Art

Medical tubes are frequently made from plasticized PVC (polyvinylchloride). However, two major disadvantages of the use of plasticized PVC are the driving forces behind the development of alternatives. Firstly, plasticized PVC has an undesired environmental impact, related to the release of dioxins and chlorine, when PVC is incinerated. Secondly, migration of toxic plasticisers, so-called "oestrogene mimics", from plasticized PVC into the human body may have a negative health effect. In addition, plasticized PVC has an insufficient thermal stability to allow for high pressure steam sterilisation in an autoclave.

An alternative for the plasticized PVC is the use of polymer compositions containing polypropylene and an elastomeric block copolymer. These compositions do not contain "oestrogene mimics". Besides the products made therefrom can be heated/molten and used anew in a new application. Additionally these compositions have an improved thermal resistance and can therefore be sterilised by high pressure steam sterilisation in an autoclave.

Kink resistant medical tubes made from a composition containing polypropylene and an elastomeric block copolymer are described in U.S. Pat. No. 3,865,776. This patent relates to kink-resistant polymeric tubing and a composition therefore. The composition comprises at least five components: a block copolymer of at least two monoalkenylarene polymer blocks and at least one hydrogenated conjugated diene polymer block having a monoalkenylarene content of 28–35 wt % and a molecular weight in the range from 20,000 to 35,000; a block copolymer of at least two monoalkenylarene polymer blocks and at least one hydrogenated conjugated diene polymer block having a monoalkenylarene content of 26–35 wt % and a molecular weight in the range from 8,000 to 155,000; a polypropylene component; a mineral white oil; and a resin component. No specific vinyl content for the hydrogenated conjugated diene polymer blocks is required and no specific type of polypropylene is required. With the described composition a tube having a diameter of about ⅜ inch (about 0.95 cm) can be manufactured that can be bent to a circumference of about nine inches (about 22.86 cm) without kinking. Although with the composition as described in U.S. Pat. No. 3,865,776 a reasonable degree of kinking resistance can be obtained, there is still room for further improvement. Furthermore it would be advantageous if kink-resistant tubes could be prepared from a composition containing less components.

Further polymer compositions containing polypropylene and a hydrogenated elastomeric block copolymer are known from Japanese patent No. 10067894. This patent describes the use of a composition, containing a polypropylene resin and an hydrogenated block copolymer for medical devices to obtain a good flexibility and clarity. The polypropylene resin can be an homopolypropylene polymer, a random polypropylene polymer or a block polypropylene polymer. The hydrogenated block copolymer contains a polyvinyl aromatic block and a polyconjugated diene block wherein the polyconjugated diene block has a high vinyl content. It will be appreciated that with the term "vinyl content" actually is meant the content of conjugated diene that is polymerised in a 1,2-manner.

According to European Patent No. 0623651, a transparent and easily processible composition for use in medical devices comprises hydrogenated polystyrene-polybutadiene-polystyrene or polystyrene-polyisoprene-polystyrene block copolymer; random polypropylene copolymer which contains, as comonomer, ethylene or butylene in concentrations of 2 to 8%; plasticiser oil; and optionally an antistatic. No specific vinyl content for the polybutadiene or polyisoprene block is required.

Japanese patent No. 10067894 and European Patent No. 0623651 do not mention the problem of kinking resistance for medical tubes. Medical tubes, however, should also be resistant to kinking in addition to good flexibility and clarity. During application, medical tubes should be able to being bent around obstacles, without kinking. Kinking involves more than just flexibility. Not all flexible tubes behave the same during bending. Some tubes can be bent without kinking, while others kink easily, drastically reducing the cross-sectional area of the tube. In medical tubes, the reduction of flow area can cause severe reduction in the flow of vital fluids. Therefore the kinking resistance is of essential importance for medical tubes.

Kink resistance is understood to be related to maintaining an increasing stress with increasing elongation. Kinking is not related to the compressive side when a tube is bent, but to the elongated side. When bending a flexible tube one reaches a certain point where further elongation occurs without resistance, also called the yield point, that is where kinking occurs. A more extensive explanation of kinking can be found in U.S. Pat. No. 3,865,776.

The object of the present invention is thus to provide medical tubes, which have an improved kinking resistance and still display a commercially attractive degree of clarity or transparency. A further object is to provide a composition for use in the production of these kink-resistant medical tubes.

SUMMARY OF THE INVENTION

The present invention relates to a kink resistant medical tube, manufactured from a polymer composition comprising:

a) a random polypropylene copolymer; and
b) a block copolymer comprising at least two vinyl aromatic polymer blocks and at least one hydrogenated conjugated diene polymer block, wherein the hydrogenated conjugated diene polymer block has a vinyl content before hydrogenation of at least 50%.

The invention further provides the use of the above mentioned polymer composition for the manufacture of medical devices having kink-resistance.

The applicant has further found that certain polymer compositions are novel and therefore the invention also provides a polymer composition comprising:

a) a random polypropylene copolymer; and
b) a block copolymer comprising at least two vinyl aromatic polymer blocks and at least one hydrogenated conjugated diene polymer block, wherein the hydrogenated conjugated diene polymer block has a vinyl content before hydrogenation in the range of 60 to 70 mol %.

DETAILED DESCRIPTION OF THE PREFERRED EMBODIMENTS

The kink resistant medical tubes according to the invention can thus be obtained by using a specific polymer composition comprising a random polypropylene copolymer and a specific block copolymer.

Component a) of the polymer composition is a random polypropylene copolymer or a mixture of random polypropylene copolymers. By a random polypropylene copolymer is understood a polymer wherein propylene monomers and one or more non-propylene alkylene co-monomers are present in a statistically random manner in the macromolecule. Suitable examples of co-monomers are ethylene, 1-butylene, 1-pentylene, 1-hexylene, 4-methyl-1-pentylene, 2-methylpropylene, 3-methyl-1-pentylene and 5-methyl-1-hexylene or mixtures of these co-monomers. Preferred co-monomers are ethylene and 1-butylene. The amount of co-monomer included may vary between wide ranges but is suitably in the range from 0.5 to 10 wt %, preferably in the range from 2 to 8 wt % and more preferably in the range from 2 to 5 wt %. Most preferably the random polypropylene copolymer is a random polypropylene copolymer containing from 2 to 8 wt % of ethylene or 1-butylene. To improve the transparency of the blend, the random polypropylene polymer can further contain a nucleating agent.

The random polypropylene copolymer should have a melt flow rate in the range of 1 to 100 dg/min, preferably between 10 and 13 dg/min. The melt flow rate is measured according to ASTM D1238.

Component b) of the polymer composition is a block copolymer or a mixture of block copolymers. The block copolymer(s) may be either linear, with a formula (A-B)n-A or (A-B)m, or branched, with a formula (A-B)pX. In these formulae A stands for a monovinyl aromatic polymer block; B stands for a hydrogenated conjugated diene polymer block; X stands for the residue of a coupling agent; n is 1 or more, preferably from 1 to 3, and most preferably 1; m is more than 1, preferably from 2 to 4 and most preferably 2; and p is more than 1, preferably from 2 to 10, more preferably from 2 to 5, most preferably from 2 to 4. Preferably component b) comprises a linear triblock copolymer (ABA). Component b) may further contain some amount of diblock (AB), to the extent that it does not interfere with the properties of the block copolymer component as a whole. The amount of diblock copolymer should be less than 50 wt % of the total block copolymer component, and more suitably be less than 30 wt %, most suitably be less than 15 wt %. Preferably component b) contains no or essentially no diblock copolymer.

The prepared block copolymer may have a tapered block structure. Each block should contain predominantly only one component, A or B. The presence of the other component than the predominant one should be less than 5 wt %, more preferably less than 2 wt %. Most preferably each block contains only one or essentially only one component, i.e. A or B.

The block copolymers, which are useful in the polymer composition according to the present invention, may be prepared by any method known in the art including the well known full sequential polymerisation method, optionally in combination with reinitiation, and the coupling method, as illustrated in e.g. U.S. Pat. Nos. 3,231,635; 3,251,905; 3,390,207; 3,598,887 and 4,219,627 and EP 0413294 A2, 0387671 B1, 0636654 A1, WO 04/22931. The block copolymer may therefore, for example, be prepared by coupling at least two diblock copolymer molecules AB together.

The coupling agent may be any di- or polyfunctional coupling agent known in the art, for example, dibromoethane, silicon tetrachloride, diethyl adipate, divinylbenzene, dimethyldichlorosilane, methyl dichlorosilane. Particularly preferred in such a preparation route is the use of non-halogen containing coupling agents, for example gamma-glycidoxypropyl-trimethoxysilane, and diglycidylether of bisphenol A.

Suitable vinyl aromatic compounds include those having 8 to 20 carbon atoms and include styrene, o-methylstyrene, p-methylstyrene, p-tert-butylstyrene, 2,4-dimethylstyrene, α-methylstyrene, vinylnaphthalene, vinyltoluene and vinylxylene, or mixtures thereof. Preferred monovinyl aromatic compounds are styrene, alpha-methylstyrene and para-methylstyrene, styrene being the most preferred. Although the average molecular weight of the vinyl aromatic polymer blocks is not restricted, the number average molecular weight is preferably within the range of 2,500 to 20,000.

Suitable conjugated dienes include those having from 4 to 8 carbon atoms, for example 1,3-butadiene, 2-methyl-1,3-butadiene (isoprene), 2,3-dimethyl-1,3-butadiene, 1,3-pentadiene and 1,3-hexadiene. Mixture of such dienes may also be used. Preferred conjugated dienes are 1,3-butadiene and isoprene. Of these, 1,3-butadiene is most preferred, because it leads to a polymer composition having advantageous low temperature properties, such as a good flexibility at low temperatures. For example, a polymer composition comprising polystyrene-hydrogenated polyisoprene—polystyrene and random polypropylene polymer in a weight ratio of 50:50 becomes brittle below temperatures of 10° C., whereas a similar polymer composition with hydrogenated polybutadiene as conjugated diene block maintains a sufficient degree of flexibility even below temperatures of −25° C. Often medical tubes and the products contained in them require storage at low temperatures. In these cases low temperature properties of the polymer composition are of essential importance. Furthermore butadiene is preferred for economical reasons, since the costs for obtaining butadiene are lower than for isoprene.

The conjugated diene polymer block should have a vinyl content before hydrogenation of at least 50%, i.e. the conjugated diene polymer block should have a vinyl content before hydrogenation of 50% or more. The optimal vinyl content may vary with the conjugated diene used and the amount of hydrogenated block copolymer used in the composition. Polybutadiene block(s) preferably have a vinyl content before hydrogenation of at least 60%, and more preferably of at least 65%. For cost-reasons increasing the vinyl content beyond 70% is not preferred. Applicant has found that increasing the vinyl content further does not increase kinking resistance or transparency to such an extent that the higher costs made to obtain this increased vinyl content can be justified. The vinyl content of the conjugated diene block(s) is therefore preferably less than 70%.

Techniques to control the vinyl content of the conjugated diene portion are well known and may involve the use of polar compounds such as ethers, amines and other Lewis bases and more in particular those selected from the group consisting of dialkylethers of glycols. Most preferred modifiers are selected from dialkyl ether of ethylene glycol containing the same or different terminal alkoxy groups and optionally bearing an alkyl substituent on the ethylene radical, such as monoglyme, diglyme, diethoxyethane, 1,2-diethoxy-propane, 1-ethoxy-2,2-tert-butoxyethane, of which 1,2-diethoxypropane is most preferred.

Although the average molecular weight of the conjugated diene blocks is not restricted, the number average molecular weight is preferably within the range of 10,000 to 150,000.

The number average molecular weights referred to in this specification and claims for component b) or constituents of component b) are measured with gel permeation chromatography (GPC) using poly(styrene) calibration standards (according to ASTM 3536). GPC is a well known method wherein polymers are separated according to molecular size, the largest molecule eluting first. The chromatograph is calibrated using commercially available polystyrene molecular weight standards. The molecular weight of other (block) polypolymers is expressed as styrene equivalent molecular weight.

After preparation, hydrogenation of the block copolymer may be accomplished using any of the methods known in the prior art. The hydrogenation will preferably be selective hydrogenation accomplished using a method such as those taught in U.S. Pat. Nos. 3,494,942; 3,634,549; 3,670,054; 3,700,633 and Re 27,145, which are incorporated herein by reference. Most preferably, selective hydrogenation will be accomplished using one of the processes taught in U.S. Pat. No. 3,700,633. These hydrogenation processes involve the use of a suitable catalyst, particularly a catalyst or catalyst precursor comprising an iron group metal compound. In the methods described in the foregoing patent documents, the catalyst is prepared by combining an iron group metal, particularly a nickel or cobalt compound with a suitable reducing agent such as an aluminium alkyl. The preferred iron group metal compounds are carboxylates and alkoxides.

The block copolymer is preferably selectively hydrogenated, thereby converting (hydrogenating) at least 80 percent, more preferably more than 98 percent and most preferably more than 99% of the initial unsaturation in the conjugated diene polymer block. Preferably, less than 10 percent and most preferably less than 2 percent of the initial unsaturation in the vinyl aromatic polymer blocks is hydrogenated to obtain the maximum benefits of hydrogenation.

The total number average molecular weight of the hydrogenated block copolymer is preferably within the range from 15,000 to 200,000, and more preferably within the range from 50,000 to 150,000 for linear block copolymers and within the range from 50,000 to 200,000 for branched block copolymers.

The vinyl aromatic content of the (total) block copolymer should be in the range from 10 to 40 wt % and is preferably in the range from 10 to 25 wt %. If the vinyl aromatic content exceeds 40% by weight, then the melt viscosity of a block copolymer is too high and it will be difficult to mix the block copolymer uniformly with the polypropylene. If the vinyl aromatic content is less than 10% by weight, the mechanical strength of the block copolymer is inadequate.

The weight ratio between component a) of the polymer composition, i.e. the random polypropylene copolymer(s), and component b) of the polymer composition, i.e. the block copolymer(s), preferably lies in the range from 80:20 to 30:70 and is more preferably in the range from 60:40 to 50:50.

The polymer composition may also, optionally, contain various additives, such as antioxidants, ultraviolet absorbers, light stabilisers or colouring agents. Preferably the amount of these additives present in the polymer composition is not more than 5 weight parts per 100 weight parts of random polypropylene and block copolymer. Medicinal oils are also frequently applied, as plastizer. Preferably the amount of medicinal oil present in a polymer composition is not more than 50 weight parts on 100 weight parts of random polypropylene and block copolymer, more preferably not more than 25 weight parts. Most preferably the polymer composition contains no or little medicinal oil.

The polymer composition can be prepared using kneading machines, such as a single screw extruder, a twin screw extruder, a Banbury mixer or a roll. The kink resistant medical tubes can be prepared from the obtained polymer composition by arbitrary methods such as injection moulding or extrusion moulding. The obtained kink resistant medical tubes are excellent in kink-resistance, while still having commercially attractive transparency. Suitable inner diameters for the obtained kink resistant medical tubes are in the range from 0.1 to 2.0 cm, more suitably in the range from 0.3 to 1.0 cm. Suitable thicknesses of the medical tube wall are in the range from 0.1 to 5 mm. Examples of the medical tubes include urinary tubes, gas delivery tubes, blood tubing and infusion tubes.

The polymer composition as described above can further be advantageously used in the manufacture of medical devices having kink resistance, other than medical tubes, such as for example kink resistant connectors between medical tubes, catheters or (blood) bags.

Certain polymer compositions useful in the manufacture of kink-resistant medical tubes are novel and the invention therefore also provides a polymer composition comprising:
a) a random polypropylene copolymer;
b) a block copolymer comprising at least two vinyl aromatic polymer blocks and at least one hydrogenated conjugated diene polymer block, wherein the hydrogenated conjugated diene polymer block has a vinyl content before hydrogenation in the range from 60 to 70%.

Although the conjugated diene can be any of the conjugated dienes mentioned hereinbefore, isoprene or butadiene are preferred and butadiene is especially preferred for the hereinabove mentioned reasons. For a polymer composition comprising butadiene in the conjugated diene polymer block(s) a vinyl content in the range from 65 to 70% before hydrogenation is preferred. Further preferences for the polymer composition are as described hereinbefore.

EXAMPLES

The invention will now be illustrated by the following non-limiting examples.

Examples 1–5 and Comparative Examples A and B

Polymer compositions 1–5 and A and B were prepared by mixing random polypropylene polymer (PP)(Montell grade EP2X29GK) with various polystyrene-hydrogenated polybutadiene-polystyrene block copolymers, varying in vinyl content in the polybutadiene block before hydrogenation, in a weight ratio of 70:30. The polystyrene-hydrogenated polybutadiene-polystyrene block copolymers had an molecular weight determined by GPC of about 100,000, were hydrogenated to a degree of more than 99% and contained about 20 wt % styrene. The final composition was sterilised by high pressure steam sterilisation in an autoclave at 120° C. during 2 hours. Of these compositions the glass transition temperature (Tg) of the polystyrene-hydrogenated polybutadiene-polystyrene block copolymers before mixing with the polypropylene polymer; the Tg of the resultant composition; the transparency of the composition and kinking of a tube prepared with the composition was determined. The Tg's were determined by DMA (Dynamic mechanical analysis) with a Rheometrics RDS-2, heating at 10° C./min, frequency 10 Hz, strain 1% on rectangular samples. Transparency was determined visually, on injection moulded test-plates and on extruded tubes 1 hour after the sterilisation test at 120° C. during 2 hour. Kinking resistance was measured on an extrusion moulded tube having an outer diameter of 7 mm and an inner diameter of 5 mm. Kinking of the tube was determined by the hand test described in U.S. Pat. No. 3,865,776. The described hand test consists of bringing the ends of a flexible tube of appropriate length together and parallel shortening the loop formed until kinking occurs and measuring the outer circumference of the loop portion of the tube. The value given represents the circumference of the loop portion of the tube where kinking starts.

Results of the tests can be found in table 1.

Example 6

Polymer composition 6 was prepared by mixing random polypropylene polymer (Montell grade EP2X29GK) with a hydrogenated polystyrene-polyisoprene-polystyrene block copolymer (Kuraray grade HVS-03) having a vinyl content in the polyisoprene block before hydrogenation of about 50%, in a weight ratio of 70:30. Results of the tests can be found in table 1.

Comparative Example C

The Polymer composition for comparative example C was prepared by mixing random polypropylene polymer (Montell grade EP2X29GK) with a polystyrene-hydrogenated random polybutadiene/styrene-polystyrene block copolymer, having a vinyl content in the midblock of about 50% and an overall styrene content of 40 wt %, of which 20 wt % is contained in the midblock, in a weight ratio of 70:30. Results of the tests can be found in table 1.

the transparency. Example 6 shows that good kinking resistance can also be obtained with a polymer composition comprising a hydrogenated polystyrene-polyisoprene-polystyrene block copolymer with a vinyl content of 50% in the polyisoprene block before hydrogenation. However, as shown by the Tg's, the composition comprising this hydrogenated polystyrene-polyisoprene-polystyrene block copolymer has a worse application temperature range. Due to the very high Tg, the blend becomes brittle below 10° C.

Comparative example C shows that although a good kinking resistance can be obtained with a polystyrene-random polybutadiene/styrene-polystyrene block copolymer, the transparency of such a composition is unacceptable.

Examples 7–11 and Comparative Example D

The polystyrene-hydrogenated polybutadiene-polystyrene block copolymer used in example 3, with a vinyl content of 69%, was mixed with random polypropylene polymer (Montell grade EP2X29GK) in several weight ratio's. The Tg of the block copolymer and the resultant polymer composition, the transparency and the kinking resistance were tested. In an comparative example also the pure random polypropylene polymer, without any block copolymer was tested. The results can be found in table 2. As can be seen from these results, both transparency as well as kinking resistance improve upon mixing with the block copolymer and good results can be obtained within a wide range of random polypropylene polymer/block copolymer weight ratio's.

TABLE 1

Variation of the vinyl content in the conjugated diene polymer block of the block copolymer.

| Example | Vinyl content of the conjugated diene polymer block before hydrogenation | Tg of the block copolymer (° C.) | Tg of the composition of block copolymer and PP (° C.) | Transparency of the composition | Kinking of the tube (cm) |
|---|---|---|---|---|---|
| A | 40 | −52 | −52/0 | moderate | 17–19 |
| B | 45 | −51 | −51/0 | moderate | 17–19 |
| 1 | 60 | −48 | −48/0 | good | 15–17 |
| 2 | 65 | −47 | −42/0 | high | 13–15 |
| 3 | 69 | −45 | −38/0 | excellent | 13–15 |
| 4 | 73 | −43 | −34/0 | excellent | 13–15 |
| 5 | 78 | −38 | −26/0 | excellent | 13–15 |
| 6 (Kuraray) | 50 | −18 | 0 (single peak) | excellent | 13–15 |
| C (S-EB/S-S) | 50 | −35 | −35/0 | non-transparent | 13–15 |

From the results in table 1 it can be seen that for good transparency and kinking resistance of the polymer composition comprising a polystyrene-hydrogenated polybutadiene-polystyrene block copolymer, a vinyl content in the polybutadiene block before hydrogenation of at least 50% is needed. Example 2 shows that the kinking resistance is further improved when the vinyl content is increased to 65%. Examples 3, 4 and 5 show that vinyl contents higher than 69% do not further improve the kinking resistance or Comparative Example E The polystyrene-hydrogenated polybutadiene-polystyrene block copolymer used in example 1, with a vinyl content of 40%, was mixed with random polypropylene polymer (Montell grade EP2X29GK) with in a weight ratio of 50:50. The Tg of the block copolymer and the resultant polymer composition, the transparency and the kinking resistance were tested. The results can be found in table 2. As can be seen from these results, the transparency of the composition is unacceptable.

TABLE 2

Effect of blend ratio random polypropylene polymer (PP)/block copolymer.

| Example | Ratio PP/block copolymer | Tg of the block copolymer (° C.) | Tg of the composition of block copolymer and PP (° C.) | Transparency of the composition | Kinking of the tube (cm) |
|---|---|---|---|---|---|
| D | 100/0 | — | 0 | moderate | 21–23 |
| 9 | 70/30 | −45 | −38/0 | excellent | 13–15 |
| 10 | 60/40 | −45 | −36/0 | excellent | 11–13 |
| 11 | 50/50 | −45 | −34/0 | excellent | 10–11 |
| 12 | 40/60 | −45 | −30/0 | excellent | 9–10 |
| 13 | 30/70 | −45 | −25/0 | excellent | 7–9 |
| E | 50/50 | −52 | −50/0 | moderate | 14–15 |

Examples 12, 13 and Comparative Example F

In Example, 12 and 13 the polystyrene-hydrogenated polybutadiene-polystyrene block copolymer used in example 3, with a vinyl content of 69%, was mixed with two different random polypropylene copolymer (Montell grade EP2X29GK and Montell grade PLZ 886) in a weight ratio of 50:50. The Montell grade EP2X29GK polypropylene copolymer also contains a nucleating agent whereas the Montell grade PLZ 886 polypropylene copolymer does not.

As a comparative example the polystyrene-hydrogenated polybutadiene-polystyrene block copolymer used in example 3, with a vinyl content of 69%, was mixed with a non-random soft polypropylene polymer (Adflex F200) in a weight ratio of 50:50. Results of the tests can be found in table 3. The results show that the composition based on EP2x29GK (Montell) has an improved transparency over the composition based on PLZ886 (Montell), because EP2x29GK (Montell) contains a nucleating agent. The use of a non-random soft polypropylene results in unacceptable low transparency and non-measurable kink resistance.

Compositions 1–14 and A–E, but not composition F, were able to withstand sterilisation at 121° C. during 2 hours, without permanent deformation occurring and with full recovery of transparency within 1 hour after sterilisation. Because of the deformation occurring during sterilisation, the kinking resistance of the composition containing Adflex F200 (example F) was not measurable.

The results can be found in table 3.

TABLE 3

Effect of the PP-type

| Example | polypropylene polymer | Tg of the block copolymer (° C.) | Tg of the composition of block copolymer and PP (° C.) | Transparency of the composition | Kinking of the tube (cm) |
|---|---|---|---|---|---|
| 12 | EP 2x29 GK (Montell) | −45 | −34/0 | excellent | 10–11 |
| 13 | PLZ 886 (Montell) | −45 | −32/0 | very high | 10–11 |
| F | Adflex F200 (soft PP, Montell) | −45 | −25 (single peak) | non-transparent | non-measurable |

Example 14

To 50 weight parts of polypropylene (EP2x29GK) and 33.3 weight parts of the polystyrene-hydrogenated polybutadiene-polystyrene block copolymer used in example 3, with a vinyl content of 69%, 16.7 weight parts of an medicinal oil (Primol 352, FDA and medical approved oil) were added. It was found that the composition had a Tg of −40/−10, an excellent transparency and kinking of the tube occurred at 10–11 cm. These results show that medicinal oils can be added to the polymer composition while still an excellent transparency and kinking resistance can be obtained.

What is claimed is:

1. A kink resistant medical tube, manufactured from a polymer composition comprising
   a) a random polypropylene copolymer; and
   b) a block copolymer comprising at least two vinyl aromatic polymer blocks and at least one hydrogenated conjugated diene polymer block, wherein the hydrogenated conjugated diene polymer block has a vinyl content before hydrogenation of at least 50 mol %;
   wherein no kinking occurs when the tube is bent to a circumference of greater than 13 cm.

2. The kink resistant medical tube according to claim 1, wherein said random polypropylene copolymer contains from 0.5 to 10 weight percent of ethylene or butylene.

3. The kink resistant medical tube according to claim 2, wherein the block copolymer is a linear triblock copolymer of the structure ABA, wherein A is a styrene polymer block and B is a hydrogenated conjugated diene polymer block.

4. The kink resistant medical tube according to claim 3, wherein the hydrogenated conjugated diene polymer block is a hydrogenated butadiene polymer block.

5. The kink resistant medical tube according to claim 4, wherein the hydrogenated butadiene polymer block has a vinyl content of from 60 to 70% before hydrogenation.

6. The kink resistant medical tube according to claim 1, wherein the weight ratio between random polypropylene copolymer and block copolymer in the polymer corriposition is from 80:20 to 30:70.

7. The kink resistant medical tube according to claim 6, also containing between 5 and 50 parts by weight of a medicinal oil per 100 parts by weight of the total weight of said block copolymer and random polypropylene copolymer.

8. The kink resistant medical tube of claim 2 wherein said random polypropylene copolymer is a propylene/ethylene copolymer having a melt flow rate of 10 to 13 dg/min as measured according to ASTM D1238.

9. The kink resistant medical tube of claim 8 wherein said random polypropylene copolymer has an ethylene content of 2 to 8 weight percent.

10. The kink resistant medical tube of claim 5 wherein the total number average molecular weight of said block copolymer is from 50,000 to 150,000.

11. The kink resistant medical tube of claim 1 wherein:
   a) said block copolymer is a linear ABA block copolymer wherein said A block is a polystyrene block, and said B block is a hydrogenated butadiene polymer block having a vinyl content of 60 to 70 mol percent prior to hydrogenation, said ABA block copolymer having a total number average molecular weight of 50,000 to 150,000; and
   b) said random polypropylene copolymer is a propylene/ethylene random copolymer having an ethylene content of 2 to 8 weight percent and a melt flow rate of 10 to 13 dg/min as measured according to ASTM D1238.

12. A kink resistant medical tube manufactured from a polymer composition consisting essentially of a) a random polypropylene copolymer having an ethylene content of 2 to 8 weight percent;

b) a block copolymer comprising at least two vinyl aromatic polymer blocks and at least one hydrogenated conjugated diene polymer block having a vinyl content before hydrogenation of 50 to 70 mol %; and c) from 0 to 50 parts by weight of a medicinal oil per 100 parts by weight of the total weight of said block copolymer and random polypropylene;

wherein no kinking occurs when the tubs is bent to a circumference of greater than 13 cm.

13. The kink resistant medical tube according to claim 12, wherein the hydrogenated conjugated diene polymer block is a hydrogenated butadiene block.

14. The kink resistant medical tube according to claim 13, wherein the hydrogenated butadiene polymer block has a vinyl content of from 60 to 70% before hydrogenation.

15. The kink resistant medical tube according to claim 13, wherein the hydrogenated butadiene polymer black has a vinyl content of from 65 to 70% before hydrogenation.

16. The kink resistant medical tube according to claim 12 wherein the weight ratio between the random polypropylene copolymer and block copolymer in the polymer composition is from 80:20 to 30:70.

17. The kink resistant medical tube according to claim 12 wherein the said block copolymer is a linear ABA block copolymer having a total number average molecular weight of 50,000 to 150,000, and wherein said A block is a polystyrene block, and said B block is a hydrogenated polybutadiene block.

18. The kink resistant medical tube according to claim 12 wherein the random polypropylene copolymer has a melt flow rate of 10 to 13 dg/min as measured according to ASTM D1238.

* * * * *